United States Patent [19]

Hubbard et al.

[11] Patent Number: 4,497,468

[45] Date of Patent: Feb. 5, 1985

[54] CATHETER PATENCY FLUSH FLOW CONTROLLER

[75] Inventors: James R. Hubbard, Moorestown, N.J.; Joseph Pelensky, Philadelphia, Pa.; Niles Kin, Clarence, N.Y.

[73] Assignee: Graphic Controls Corporation, Buffalo, N.Y.

[21] Appl. No.: 371,656

[22] Filed: Apr. 26, 1982

[51] Int. Cl.³ .............................................. F16K 47/04
[52] U.S. Cl. .................................... 251/117; 251/322; 604/249
[58] Field of Search ............... 251/117, 118, 347, 348, 251/322, 323, 214; 604/249

[56] References Cited

U.S. PATENT DOCUMENTS

| | | | |
|---|---|---|---|
| 1,417,510 | 5/1922 | Gauger et al. | 251/322 X |
| 1,506,434 | 8/1924 | Leins | 251/117 |
| 2,243,930 | 6/1941 | Watson | 251/322 |
| 3,479,007 | 11/1969 | Buell | 251/214 |
| 4,084,609 | 4/1978 | Johnson | 251/322 X |
| 4,192,303 | 3/1980 | Young et al. | 251/117 X |
| 4,291,702 | 9/1981 | Cole et al. | 251/117 X |

*Primary Examiner*—Arnold Rosenthal
*Attorney, Agent, or Firm*—Ratner & Prestia

[57] ABSTRACT

Catheter patency flow-flush controller comprising push-button valve mechanism with fast flow flush path surrounding the valve member, normally closed by a valve element and valve seat interposed between the inlet and outlet of the internal passageway of the controller by a coil spring located external of the internal passageway, the coil spring also compressively retaining a resilient seal at all times about the entry way through which the valve plunger enters the controller internal passageway. Preferably, the valve member push-button actuator includes a top cap member with dependent skirt which serves also as an alignment guide during valve movement by sliding engagement with an upwardly open skirt associated with the controller housing. Other features of the invention are also disclosed and claimed.

16 Claims, 4 Drawing Figures

CATHETER PATENCY FLUSH FLOW CONTROLLER

BACKGROUND OF THE INVENTION

This invention pertains to a catheter patency flush flow controller and particularly to a push-button type flush flow controller wherein, during both the slow flow and fast flush mode, the internal space of the controller is positively sealed against both inward and outward leakage.

An in-dwelling vascular catheter may be used for clinical monitoring of blood system pressure at a particular point in the vascular network and for the study of related parameters including arterial pulse wave form, stroke volume, heart rate, cardiac output, duration of systole, and systolic, diastolic, and mean blood pressure. For pressure monitoring through the catheter, the catheter must be kept filled with liquid and free of contaminants and gas bubbles. In addition, the tendency of blood to clot at the tip of the catheter must be prevented, typically by maintaining a very slight positive pressure of a saline fluid which fills the catheter and flows through the catheter, through its tip and into the blood stream at a very slow and well controlled rate, on the order of 2-4 milliliters per hour. From time to time, the catheter must be flushed, with a high rate flow, on the order of 150-400 milliliters per minute, of saline fluid, in order to eliminate gas bubbles, flush contaminants and otherwise maintain the patency of the catheter and the continuity of the fluid contained therein.

A variety of apparatus has been devised for this purpose, gradually evolving through a system including multiple path and stopcock connections between a saline fluid source and the catheter (as in U.S. Pat. No. 3,581,733—Grandjean). Subsequently, a number of catheter patency flow-flush controllers have been devised with a fail-safe valve, for the flush mode, either in a bypass passageway, as in U.S. Pat. No. 3,675,891—Reynolds et al, or with various types of push-button valve actuations, with the valve spring loaded in the flush path closed position, as seen for example in U.S. Pat. No. 4,200,119—Cunningham, U.S. Pat. No. 4,210,178—Morse et al, and U.S. Pat. No. 4,291,702—Cole et al. Still another fail-safe multiple passageway configuration is seen in U.S. Pat. No. 4,192,303—Young et al.

A further patent cited in the prosecution of U.S. Pat. No. 3,675,891 is U.S. Pat. No. 1,983,227—Hall et al. The Hall et al patent discloses a gas pilot light control including a high rate flow path for pilot lighting and a low rate continuous flow path for normal pilot light maintenance, in which a push-button valve is utilized to open the fast flush path. The push-button valve shown in the Hall et al patent is somewhat similar to that utilized in the present invention.

Still another push-button design is embodied in a catheter patency flow-flush controller sold by the American Medical Products Corporation. In this controller, the push-button valve actuator comprises a plunger with an enlarged cross section valve closing portion, biased upwardly against a valve seat in the internal passageway of the device, by a coil spring disposed within the valve housing and at the end of the valve plunger. The slow flow capillary passageway extends through the center of this valve plunger in the American Medical Products device. Leakage into and out of the internal passageway of the controller in the American Medical Products device is prevented by an O-ring surrounding the valve plunger at its entry into the valve housing. (A cross-sectional sketch of this device is submitted, for purposes of examination, with this application but should not otherwise be considered part of the application.)

Notwithstanding these prior developments in the field of catheter patency flush flow controllers, there remains a continuing need for, and it is the general object of this invention to provide, controllers improved in one or more, and preferably all, of the following respects: positive leak prevention in all operational modes; simplified internal configuration to minimize formation of gas bubbles; fail-safe valve design, which facilitates proper finger actuation with one hand and a minimum of visual observation, which minimizes the possibility of inadvertent actuation and which precludes valve malfunction through valve misalignment or disassembly.

It is also an object to provide a catheter patency flow-flush controller with these improved functional features, which is also improved with respect to ease of manufacture and is safer due to reduced likelihood of manufacturing and assembly defects.

BRIEF DESCRIPTION OF THE INVENTION

This general object is met, in accordance with the present invention, by catheter patency flush flow controller including a valve housing with an internal passageway and inlet and an outlet thereto, the inlet and outlet displaced from one another along a valve actuation line with a valve seat therebetween. An actuation valve disposed in the passageway includes a valve element normally biased into a valve closed position at the seat, with a slow flow passageway through the valve element by-passing the valve seat.

The actuating valve comprises a push-button plunger biased upwardly by a coil spring surrounding the plunger and located externally of the fluid passageway through the controller housing. The plunger entry into the housing is sealed by a resilient member, such as an O-ring, held in compression at all times, by the coil spring.

In the preferred form of the invention, the push-button plunger includes an overcap with dependent skirt mating with an upwardly open skirt from the controller housing so as to serve as a guide maintaining the plunger in alignment. Further, plunger alignment is maintained by dimples on the internal passage of the controller housing.

Other details of the invention may be seen in the drawings, and these details, as well as the invention generally, may be better understood from the detailed description thereof which follows, taken in conjunction with the appended claims and the drawings, in which:

DETAILED DESCRIPTION OF THE INVENTION

Figure 1:
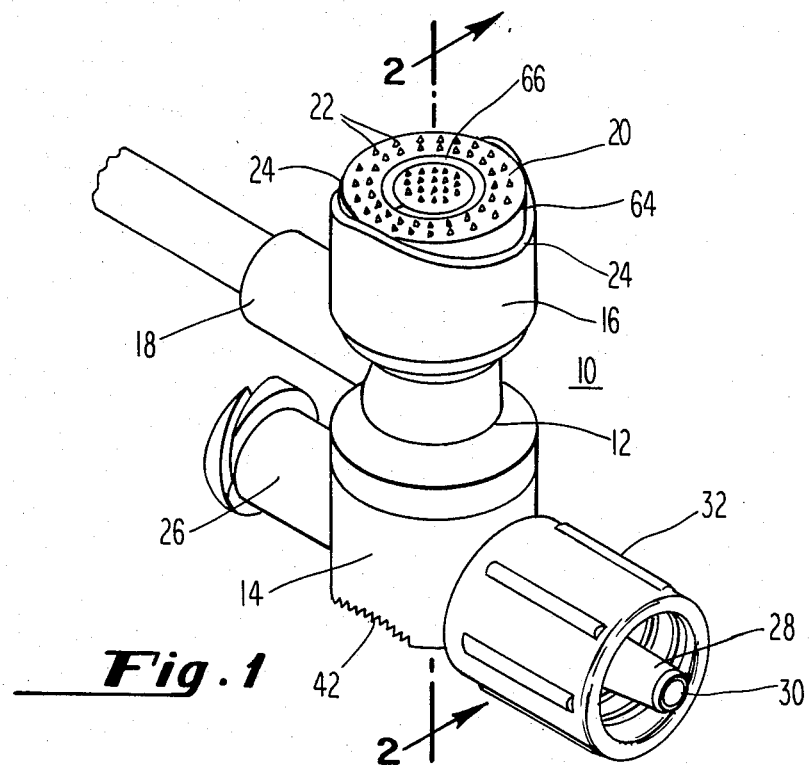
FIG. 1 is a perspective view of the catheter patency flush flow controller of the present invention in its preferred embodiment.

Referring more specifically to FIG. 1, there is shown a catheter patency flow-flush controller 10 comprising the preferred embodiment of the present invention. Controller 10 includes an upper housing 12 and a lower housing 14, upper housing 12 including an upwardly open skirt 16 and an inlet fitting 18. Disposed within upwardly open skirt 16 is a push-button valve actuator 20 with surface dimples 22, to enable a user to better feel the valve actuation surface. Valve actuator 20 is shown in its normal rest position, substantially surrounded by upwardly open skirt 16, which thereby serves as a guard to prevent inadvertent actuation of the push-button means. At two points along the top periphery of upwardly open skirt 16, the top edge includes a downward relief feature 24 to provide access for an actuation finger.

Lower housing 14 includes lockable outlets 26 and 28, outlet 28 including a central tubular projection 30, surrounded by an internally threaded female oversleeve 32.

Figure 2:
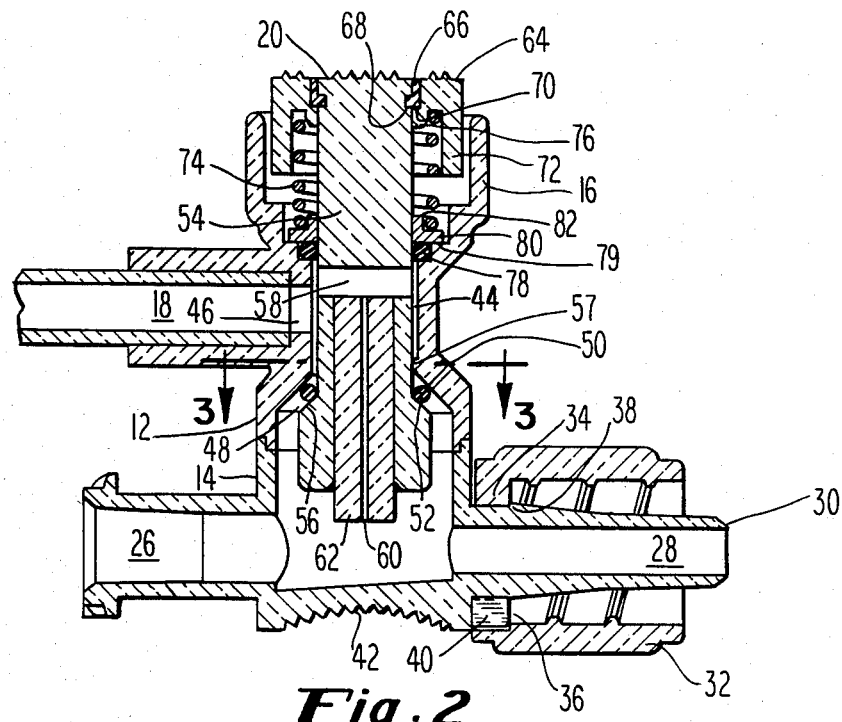
FIG. 2 is a cross-sectional view of the controller shown in FIG. 1, in the plane 2—2 of FIG. 1.

Referring specifically now to FIG. 2, oversleeve 32 includes an annular disk closure element 34 having a keyway 36 at one circumferential point, with the annular disk closure 34 blocked between the wall of lower housing 14 and a circumferential abutting shoulder 38 on the outer periphery of central tubular projection 30. Oversleeve 32 is locked against rotational movement by a key 40 extending from lower housing 14.

Lower housing 14 further includes concave bottom surface 42, oppositely disposed, with respect to valve actuator 20, and ridged to facilitate a finger feel for the proper finger position for valve actuation and to facilitate proper valve actuation, all with one hand, while minimizing the need for visual observation by the user, often a doctor or nurse, concurrently occupied with other concerns.

Internally, lower housing 14 forms a valve outlet plenum adapted to communicate through outlets 26 and 28 with an in-dwelling vascular catheter and a pressure sensing means. During normal operation, all of the internal space of controller 10 and outlets 18, 26, and 28 is occupied by a fluid, such as a saline solution.

As best seen in FIG. 2, the controller housing includes an internal passage with an inlet 46 and an outlet 48, between which is disposed a valve seat 50, including in this the preferred embodiment of the invention, an O-ring sealing means 52.

Figure 3:
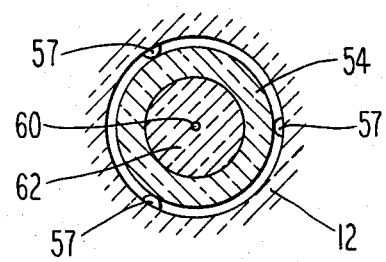
FIG. 3 is a detailed cross-sectional view of one part of the controller shown in FIGS. 1 and 2, taken in the plane 3—3 of FIG. 2.

Disposed within internal passage 44 is valve member 54 including an enlarged cross section valve element 56, adapted to be biased upwardly into a valve closed position against valve seat 50 and O-ring seal 52. Valve member 54 is of slightly smaller cross section in its segment between inlet and outlet openings 46 and 48, so as to permit fluid passage around the periphery thereof. Alignment within the passageway is maintained, however, in the preferred embodiment of the invention by dimples 57 circumferentially displaced about valve member 54 and across the fluid passageway space around the periphery thereof, as shown in FIG. 3.

A slow flow (on the order of 2–4 milliliters per hour) flow path through valve member 54 is provided by cross bores 58 opening into a central capillary passageway 60 of a glass tube insert 62 in the center of valve member 54. Glass tube insert 62 with central capillary passageways 60 is sometimes referred to as a marine bore capillary and may consist of a piece of a glass thermometer tube.

Valve actuator 20 comprises the topmost exterior surface of valve member 54, together with the top surface of a surrounding cap member 64 locked in place in a fail-safe mode by a split ring key 66 fitting in a mating groove 68 on the periphery of valve member 54 and in a shoulder 70 on the inner circumference of cap 64.

Cap 64 further includes a dependent skirt 72 fitting within and mating for sliding engagement with upwardly open skirt 16 ensuring, together with dimples 57, positive alignment of valve member 54 throughout its valve actuation movement along its actuation line (vertical as shown in FIGS. 1 and 2). In this manner, canting or misalignment failure of the valve is prevented.

Valve member 54 is biased upwardly (as seen in FIG. 2) into a fast flow path closed valve position, as seen in FIG. 2, by coil spring 74 retained under compression between cap 64 and an abutment 79 of upper housing 12 facing the lower surface of cap 64, and surrounding the opening into passageway 44 through which valve member 54 enters. To maintain proper alignment of coil spring 74, cap 64 also includes a circumferential spacer 76, about which one end of coil spring 74 fits.

At its lower end, coil spring 74 holds a resilient sealing means, namely O-ring 78 under compression at all times, to prevent leakage of saline fluid from the internal passageway of housing 12, and also to prevent inward leakage of air or contaminants into fluid within controller 10.

Preferably, O-ring 78 is compressively retained by spring 74 through a circumferential washer 80 including a perpendicularly disposed cylindrical extension 82, about which is seated the lower end of coil spring 74.

In operation, saline fluid would normally be supplied from a controlled positive pressure supply source thereof to inlet 18 of controller 10. Under the positive pressure supply, saline fluid would flow through capillary passageway 60 and exit outlet 28, at a controlled flow rate on the order of 2–8 milliliters per hour to an in-dwelling vascular catheter connected to outlet 28. Internal pressure at the outlet of the in-dwelling vascular catheter would be transmitted back through saline fluid in the in-dwelling catheter and outlet 28 to the plenum in lower housing 14 of controller 10 and through outlet 26 to a pressure sensing means, typically a transducer, connected thereto. Other intermediate mechanisms, such as a vent valve, may be interposed between outlet 26 and the pressure sensing means. Outlets 26 and 28 are, of course, functionally interchangeable and the elements connected therewith may also be interchanged.

Periodically, when it is desired to secure a fast flow saline fluid through the in-dwelling vascular catheter, the valve means of controller 10 is actuated by finger pressure on valve actuator 20, normally actuated with one hand operation and a resistant force through the thumb asserted on lower surface 42. Under the finger actuation pressure, valve member 54 is moved downwardly, unseating valve element 56 and permitting a relatively fast flow, on the order of 150–400 milliliters per minute of saline fluid through passageway 44, past valve seat 50 and to the outlet plenum downstream of valve seat 50. Upon release of the finger actuation pressure, valve member 54 returns to its valve-closed upwardly biased position. The controlled slow flow rate of saline fluid through outlet 28 is then resumed.

Figure 4:
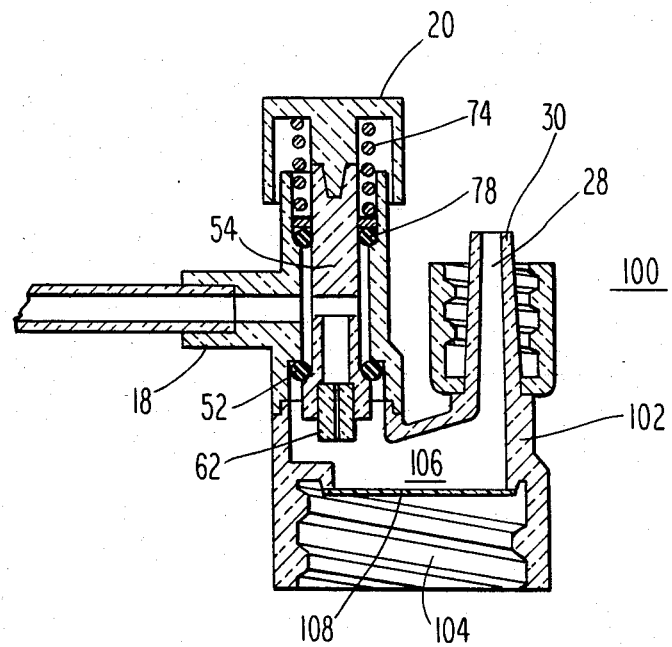
FIG. 4 is a cross-sectional view of a modified form of the controller of the present invention, including an integral transducer mounting.

In the alternative embodiment of the invention shown in FIG. 4, wherein like elements otherwise bear like reference numerals, controller 100 includes a lower housing 102 including a pressure sensor receiver housing 104, adapted to receive, for example, a transducer with a pressure-sensing forward surface. Interposed between the internal space of adapter 104 and the plenum space 106 of lower housing 102 is a pressure transmitting membrane 108 adapted to isolate the housing space on either side thereof. Adapter 104 is designed to receive a transducer with a forward pressure-sensing surface in pressure-sensing communication with, preferably in physical contact with, membrane 108.

Thus, in the embodiment of the invention shown in FIG. 4, the catheter patency flow-flush controller of this invention includes an integral pressure sensor housing means to facilitate connection of the controller to the pressure sensing means, which nevertheless isolates the pressure sensor so as to obviate the need for sterilization thereof.

While this invention has been described with reference to specific embodiments thereof, it is not limited thereto. Instead, the claims which follow are intended to be construed to encompass not only the forms and embodiments of the invention shown and described, but also such other forms and embodiments and such variants and modifications thereof as may be devised by those skilled in the art without departing from the true spirit and scope of the present invention as may be ascertained from the foregoing description and accompanying drawings.

I claim:

1. A catheter patency flow-flush controller adapted for connection to an in-dwelling vascular catheter and for selective delivery thereto of a patency-maintaining fluid at one of two pre-selected rates, said controller including:
   (a) a housing having at least one passage therethrough, said housing also having two openings, linearly displaced from one another along a valve actuation line, said openings communicating with said passage and comprising an inlet and an outlet for said passage;
   (b) a valve seat defined in said passage between said openings;
   (c) a valve member mounted in said passage and movable along said valve actuation line;
   (d) means for biasing a valve element of said valve member into valve-closing contact with said valve seat;
   (e) internal valve passage extending through said valve member for providing a continuous low flow rate, liquid flow path through said valve member from said inlet to said outlet of said housing;
   (f) push button means for selectively moving said valve member out of contact with said valve seat to provide a high rate liquid flow path around said valve member from said inlet to said outlet;
   said controller characterized by
   (g) said biasing means consisting of a coil spring axially aligned with said valve actuation line and retained under compression between (i) a first abutment formed in a portion of said housing surrounding said valve member, said first abutment including a resilient sealing means held under compression by said spring and adapted to prevent leakage around said valve member at said first abutment, and (ii) a second abutment, facing said first abutment, and associated with said valve member;
   (h) said valve member further including a cap member with a downwardly dependent skirt mating with and secured to said valve member, said cap member forming said second abutment and said dependent skirt surrounding at least part of said coil spring, said cap member and valve member together forming said push button means,
   (i) said housing further including an upwardly dependent open skirt oppositely disposed with respect to said dependent skirt of said cap, said housing skirt also surrounding at least part of said coil spring, said housing skirt and said cap dependent skirt fitting within one another in mating portions thereof and being slidably movable relative to one another along said valve actuation line within said mating portion, wherein said valve member is cylindrical, and said first abutment resilient sealing means is an O-ring compressively retained against said valve member and against a portion of said first abutment by said coil spring, said cap and second abutment including a circumferential spacer surrounding said valve member, one end of said coil spring fitting around said circumferential spacer, said controller further including, interposed between the end of said coil spring and said first housing abutment O-ring, a washer having a planar element surrounding said valve member and positioned and adapted to transmit compressive force from said spring to said O-ring, said washer also having a cylindrical element perpendicularly disposed with respect to said planar element, said cylindrical element slidably engaging said valve member, said spring end fitting around said cylindrical element.

2. A controller, as recited in claim 1, wherein said cap member includes a central opening corresponding in shape and fit around the cross-sectional shape of said valve member, said cap member and valve member being locked together by a key mating with a circumferential channel on the outer periphery of said valve member and a circumferential groove on the inner periphery of said cap member opening.

3. A controller, as recited in claim 2, wherein said key is a split ring for ease of assembly.

4. A controller, as recited in claim 2, wherein said housing open skirt substantially surrounds said cap dependent skirt, in the normal rest position of said push button means.

5. A controller, as recited in claim 4, wherein said valve member, cap surface valve actuation surface is essentially flat and the end of said housing open skirt is relieved slightly, the unrelieved portion adapted to serve as a guard to prevent inadvertent actuation of said push button means, the relieved portion adapted to facilitate finger access and finger actuation of said push button means, at at least one circumferential portion of said housing skirt.

6. Controller, as recited in claim 1, wherein said housing passage and valve member include guide means for maintaining the alignment of said valve member in said passage along said valve actuation line, said guide means comprising circumferentially distributed dimples on the inner surface of said housing passage and a portion thereof facing said valve member.

7. Controller, as recited in claim 6, wherein said guide means comprise circumferentially distributed dimples on the inner surface of said housing passage in a portion thereof facing said valve member.

8. Controller, as recited in claim 4, wherein said housing passage comprises a tubular segment, at one end of which is disposed said first housing abutment, at the other end of which is disposed a passageway enlargement forming said valve seat and at an intermediate location of which is disposed the first of said openings, and a portion of said valve member disposed within said tubular segment having a cross section such that a fluid flow space is provided between said valve member and the interior surface of said passage.

9. Controller, as recited in claim 8, wherein said valve element comprises an enlarged segment of said valve member, adapted to be urged toward and into sealingly mate with said valve seat to prevent fluid flow past said valve seat.

10. Controller, as recited in claim 9, wherein said housing passage includes a plenum chamber in communication with said first opening, said valve seat being disposed within said passage between said plenum chamber and said first opening.

11. Controller, as recited in claim 10, wherein said plenum chamber includes said second opening and a third opening, said second and third openings including fittings adapted to be connected to an in-dwelling vascular catheter and to a pressure sensor, respectively.

12. Controller, as recited in claim 11, wherein one of said fittings includes a centrally disposed tubular projection extending from said plenum chamber, said projection including a circumferential shoulder about its outer periphery and a key located at one point thereon, said one fitting further including an internally threaded female oversleeve, surrounding said central tubular projection, said female oversleeve including an annular end disk having a key way adapted to mate with one another whereby said end disk is retained between said shoulder and said plenum chamber and said sleeve is locked from circumferential movement by said key and key way.

13. Controller, as recited in claim 10, wherein said plenum chamber includes a sensor fitting adapted to receive a pressure sensor with a forward pressure sensing surface, and a pressure transmitting membrane interposed between said plenum chamber and said sensor fitting, said member being disposed so as to be in pressure tansmitting relationship with said forward pressure sensing surface of said sensor as it is received in said sensor fitting.

14. Controller, as recited in claim 11, wherein said fittings extend perpendicularly from said valve actuation line and the exterior surface of said plenum chamber which is intersected by said valve actuation line is concave and is thereby adapted to receive a finger grip opposite that of said push-button valve actuation means.

15. Controller, as recited in claim 14, wherein said concave exterior plenum chamber surface and the oppositely disposed exterior surface of said push-bottom valve actuation means is dimpled or ridged to be self-indicative of proper finger position for valve actuation.

16. A catheter patency flow-flush controller adapted for connection to an in-dwelling vascular catheter and for selective delivery thereto of a patency-maintaining fluid at one of two pre-selected rates, said controller including:
 (a) a housing having at least one passage therethrough, said housing also having two openings, linearly displaced from one another along a valve actuation line, said openings communicating with said passage and comprising an inlet and an outlet for said passage;
 (b) a valve seat defined in said passage between said openings;
 (c) a valve member mounted in said passage and movable along said valve actuation line;
 (d) means for biasing a valve element of said valve member into valve-closing contact with said valve seat;
 (e) internal valve passage extending through said valve member for providing a continuous low flow rate, liquid flow path through said valve member from said inlet to said outlet of said housing;
 (f) push button means for selectively moving said valve member out of contact with said valve seat to provide a high rate liquid flow path around said valve member from said inlet to said outlet;
said controller characterized by
 (g) said biasing means consisting of a coil spring axially aligned with said valve actuation line and retained under compression between (i) a first abutment formed in a portion of said housing surrounding said valve member, said first abutment including a resilient sealing means held under compression by said spring and adapted to prevent leakage around said valve member at said first abutment, and (ii) a second abutment, facing said first abutment, and associated with said valve member.
 (h) wherein said valve member is cylindrical, and said first abutment resilient sealing means is an O-ring compressively retained against said valve member and against a portion of said first abutment by said coil spring,
 (i) wherein said cap and second abutment include a circumferential spacer surrounding said valve member, one end of said coil spring fitting around said circumferential spacer,
 (j) said controller further including, interposed between the end of said coil spring and said first housing abutment O-ring, a washer having a planar element surrounding said valve member and adapted to transmit compressive force from said spring to said O-ring, and
 (k) said washer also having a cylindrical element perpendicularly disposed with respect to said planar element, said cylindrical element slidably engaging said valve member, said spring end fitting around said cylindrical element.

* * * * *